United States Patent [19]

Sasaki et al.

[11] Patent Number: 4,965,393
[45] Date of Patent: Oct. 23, 1990

[54] PROCESS FOR PRODUCING ACRYLONITRILE

[75] Inventors: Yutaka Sasaki; Kunio Mori; Kiyoshi Moriya, all of Kanagawa, Japan

[73] Assignee: Nitto Chemical Industry Co., Ltd., Tokyo, Japan

[21] Appl. No.: 318,299

[22] Filed: Mar. 3, 1989

[30] Foreign Application Priority Data

Mar. 3, 1988 [JP] Japan ................................ 63-48694

[51] Int. Cl.$^5$ ........................................... C07C 253/26
[52] U.S. Cl. .................................................. 558/324
[58] Field of Search ........................................ 558/324

[56] References Cited

U.S. PATENT DOCUMENTS

| Re. 32,484 | 8/1987 | Grasselli et al. | 558/324 X |
| 4,377,534 | 3/1983 | Grasselli et al. | 558/324 X |
| 4,757,038 | 7/1988 | Sasaki et al. | 558/324 X |

FOREIGN PATENT DOCUMENTS

| 2258821 | 6/1973 | Fed. Rep. of Germany . |
| 2424934 | 1/1975 | Fed. Rep. of Germany . |
| 2732952 | 2/1978 | Fed. Rep. of Germany . |

OTHER PUBLICATIONS

Kirk-Othmer, "Encyclopedia of Chemical Technology", 3rd-ed., vol. 6, p. 489, (1979).
Kirk-Othmer, "Encyclopedia of Chemical Technology", 3rd-ed., vol. 15, pp. 795-796 (1981).

*Primary Examiner*—Joseph Paul Brust
*Attorney, Agent, or Firm*—Sughrue, Mion, Zinn, Macpeak & Seas

[57] ABSTRACT

A process for producing acrylonitrile by the vapor-phase catalytic ammoxidation of propylene using a catalyst whose composition is represented by the empirical formula (I):

$$P_qR_rMo_{10}Bi_aFe_bSb_cNi_dO_e \qquad (I)$$

where
R is Na and/or K;
subscripts q, r, a, b, c, d and e represent atomic ratios, and when the atomic ratio of Mo is 10, q=0 to 3, r=0.01 to 1.5, a=0.1 to 3, b=0.1 to 2.5, c=5 to 30, d=4 to 8, and e=a number corresponding to the oxide formed by chemical combination of the above-described components.

8 Claims, No Drawings

PROCESS FOR PRODUCING ACRYLONITRILE

FIELD OF THE INVENTION

The present invention relates to a process for producing acrylonitrile by the vapor-phase catalytic ammoxidation of propylene. More particularly, the present invention relates to a process for producing acrylonitrile by the vapor-phase catalytic ammoxidation of propylene using a Mo-Bi-Fe-Sb-Ni-alkali metal (Na and/or K) based catalyst which not only has high reactivity with propylene but also ensures high acrylonitrile yield.

BACKGROUND OF THE INVENTION

Various catalysts have been proposed for use in the production of acrylonitrile by ammoxidation of propylene. In particular, substantial efforts have been made in the development of Mo—Bi base catalysts and a number of multi-component catalysts of this system have been proposed. Approaches directed to the refinement of these catalysts are described in many patents including: JP-B-No. 36-5870 (corresponding to U.S. Pat. No. 2,904,580) (the term "JP-B" as used herein means an "examined Japanese patent publication"), JP-B-No. 38-17967 (corresponding to U.S. Pat. No. 3,226,422), JP-B-No. 39-8512, JP-B-No. 45-35287, JP-A-48-47476 (the term "JP-A" as used herein means an "unexamined published Japanese patent application"), JP-B-No. 51-33888 (corresponding to U.S. Pat. No. 4,503,001), JP-B-No. 57-65329, JP-B-No. 58-2232 (corresponding to U.S. Pat. No. 4,228,098), JP-B-No. 59-16817 (corresponding to U.S. Pat. No. 4,290,922), JP-B-No. 60-36812 (corresponding U.S. Pat. Nos. 4,377,534 and 4,162,234), JP-B-No. 61-26419 (corresponding to U.S. Pat. No. 4,443,556), and JP-B-No. 61-58462 (corresponding to U.S. Pat. No. 4,600,541).

The improved catalysts described in these prior patents are based on the combination of Mo, Bi and Fe and further contain catalyst components selected from expensive elements such as Co, rare earth elements and nobel metal elements. Because of the use of such expensive elements, these catalysts successfully provide fairly high yields of acrylonitrile. However, it has been difficult for Mo—Bi base catalysts to ensure adequately high acrylonitrile yields in the absence of those expensive catalyst components.

SUMMARY OF THE INVENTION

An object, therefore, of the present invention is to provide a process for producing acrylonitrile in high yield by the vapor-phase catalytic ammoxidation of propylene using a Mo—Bi—Fe—Sb—Ni—Na and/or K based multi-component catalyst that does not contain an expensive catalyst component such as Co, a rare earth element or a noble metal element and yet which ensures high catalytic activity.

The object of the present invention can be attained by a process for producing acrylonitrile by the vapor-phase catalytic ammoxidation of propylene using a catalyst whose composition is represented by the empirical formula (I):

$$P_q R_r Mo_{10} Bi_a Fe_b Sb_c Ni_d O_e \qquad (I)$$

wherein

R is Na and/or, K preferably K or a mixture of Na and K;

the subscripts q, r, a, b, c, d and e represent atomic ratios, and when the atomic ratio of Mo is 10, q=0 to 3,
r=0.01 to 1.5,
a=0.1 to 3,
b=0.1 to 2.5,
c=5 to 30,
d=4 to 8, and
e=a number corresponding to the oxide formed by chemical combination of the above-described components.

DETAILED DESCRIPTION OF THE INVENTION

The vapor-phase ammoxidation of propylene is an established technology in the art and can be performed by any known technique as described, for example, in U.S. Pat. Nos. 3,226,422 and 4,503,001 as long as it is not detrimental to the purposes of the present invention. In the present invention, this reaction is carried out in the presence of either an oxide composition that is composed of Mo, Bi, Fe, Sb, Ni, and Na and/or K or an oxide composition that additionally contains a phosphorus component.

A main aspect of the present invention lies in the catalyst used, which may be any catalyst that has the composition represented by the empirical formula (I) noted above. The atomic ratios of the respective components of this catalyst which are particularly preferred for the purpose of providing improved acrylonitrile yield are as follows: when the atomic ratio of Mo is assumed to be 10, q=0 to 1.5, r=0.05 to 1.0, a=0.5 to 2.5, b=0.5 to 2, c=6 to 28 (more preferably, c=8 to 25), and d=4.5 to 7.5.

It is not completely clear what compound is formed of the respective catalyst components, i.e., the Mo, Bi, Fe, Sb, Ni, and Na and/or K, and optional P, and in what way such compound contributes to improvements in the activity and physical properties of the resulting catalyst. While not desiring to be found, it is postulated that the constituent elements of the catalyst are closely interrelated in terms of the ability of the catalyst to exhibit its intended effect. If the composition of the catalyst is outside the range specified by the empirical formula (I) set forth above, a reduced selectivity of the catalyst for acrylonitrile or impaired physical properties of the catalyst or other problems will occur making it difficult to attain the objects of the present invention. A particularly important component is antimony and when the atomic ratio of Mo is 10, the atomic ratio of Sb must be within the range of 5 to 30 so that its addition will prove most effective for not only increasing the conversion to acrylonitrile but also contributing to an improvement in the physical properties of the catalyst. By adding Sb in an amount within the stated range, the reproducibility of the catalyst can also be improved. If the nickel component of the catalyst is replaced by Co which is also a Group VIII element, the selectivity for acrylonitrile is decreased.

Catalysts having the composition represented by the empirical formula (I) set forth herein can be prepared by any known methods as described, for example, in U.S. Pat. Nos. 3,044,965, 3,746,657 and 4,040,978 and it is particularly desirable that the respective components of the catalyst are intimately mixed in a homogeneous structure.

Suitable starting materials for the components of the catalyst to be used in the present invention may be selected from among many compound forms of the components including the oxides, hydroxides, chlorides and nitrates thereof.

Suitable starting materials for the Mo component may be selected from molybdenum oxides such as molybdenum trioxide, molybdic acid, ammonium paramolybdate, ammonium metamolybdate, and molybdenum-containing heteropolyacids such as phosphomolybdic acid and silicomolybdic acid, and the salts thereof.

Appropriate starting materials for the Bi component may be selected from bismuth salts such as bismuth nitrate and bismuth sulfate, bismuth trioxide, and the metallic bismuth dissolved in nitric acid.

Typical starting materials for the Fe component may be selected from ferrous oxide, ferric oxide, tri-iron tetroxide, iron nitrate and metallic iron dissolved in heated nitric acid.

Suitable starting materials for the Sb component are antimony trioxide, antimony tetroxide and antimony pentoxide.

Illustrative starting materials for the nickel component are nickel oxide, nickel hydroxide, and nickel nitrate.

Suitable starting materials for the phosphorus component are phosphorous acid, phosphoric acid, and salts thereof such as ammonium phosphates and alkali metal phosphates.

Preferred examples of the starting materials for component R, namely, sodium or potassium, include the nitrates, carbonates, hydroxides, oxides and chlorides of the respective elements.

The starting, materials described above are intimately mixed in desired proportions and the mixture is dried at a temperature in the range of 50° to 200° C. for less than 20 hours and calcined to prepare a catalyst for use in the present invention. The clacination conditions are important for imparting the desired activity to the catalyst, and the catalyst mixture is preferably heated in a non-reductive atmosphere at a temperature in the range of about 200° to about 800° C., preferably 400° to 750° C., for a period of about 0.5 to about 10 hours.

The catalyst may be employed either in the absence or in the presence of a support as a catalyst carrier. When a catalyst support is employed, a preferred amount of support is in the range of from about 10 to about 90 wt % of the total catalyst weight. Suitable supports include silica, alumina, zirconia, silica-alumina, silicon carbide, alundum, and inorganic silicates, most preferably silica.

The catalyst may be in the form of pellets, tablets, spheres, granules or any other shape of a desired size depending upon the specific use of the catalyst.

The catalyst may be used in the present invention either as a fixed bed system or a fluidized bed system as described, for example, in U.S. Pat. Nos. 4,290,922 and 4,503,001. When used in a fixed bed system, the catalyst is around several millimeters in size, while the catalyst particles of 20 to 200 μm in size are used in a fluidized bed system.

The process of the present invention is performed by supplying propylene, ammonia and oxygen to a reactor packed with the so prepared catalyst. For economic reasons, air is preferably used as an oxygen source. Air may be enriched with a suitable amount of oxygen, if desired.

The molar ratio of oxygen to propylene in the feed to the reactor is in the range from about 1:1 to 4:1, but a comparatively low molar ratio in the range of from about 1.5:1 to about 2.5:1 may be employed since the catalyst used has a high selectivity for acrylonitrile. The molar ratio of ammonia to propylene in the feed may be adjusted within the range of from about 0.8:1 to about 3:1, with the range of from about 0.9:1 to about 1.5:1 being preferred. If desired, an inert gas such as nitrogen or water vapor may be supplied to the reactor. The content of inert gas in the feed gas is in the range of from zero to 99 percent by volume.

The reaction temperature is preferably within the range of from about 380° to about 500° C., with the range of from about 400° to about 480° C. being particularly preferred. A suitable reaction pressure is within the range of from an atmospheric pressure to about 3 kg/cm$^2$.G The apparent catalytic contact time is suitably within the range of from about 1 to about 30 seconds, with the range of from about 2 to about 20 seconds being particularly preferred.

The following examples are provided for the purpose of further illustrating the present invention but are in no way to be taken as limiting the present invention.

In the examples, the catalyst activity was evaluated by performing a reaction with a gas of the following composition being supplied into a catalyst-packed fluid-bed type reactor whose fluidized bed portion had an inside diameter of 2.5 cm and a height of 40 cm; the reaction pressure was atmospheric:

Oxygen(supplied as air)/propylene=2.0 (mol/mol)
Ammonia/propylene=1.3 (mol/mol).

The acrylonitrile yield and propylene conversion as set forth herein are respectively defined by:

Acrylonitrile Yield (%) =

$$\frac{\text{Carbon Weight of Acrylonitrile Product}}{\text{Carbon Weight of Propylene Feed}} \times 100$$

Propylene Conversion (%) =

$$\frac{\text{Carbon Weight of Consumed Propylene}}{\text{Carbon Weight of Propylene Feed}} \times 100$$

EXAMPLE 1

A catalyst having the empirical formula $K_{0.4}Mo_{10}Bi_{1.5}Fe_{10}Sb_{15}Ni_{6.5}O_{70.45}(SiO_2)_{60}$ was prepared by the following procedures.

Potassium nitrate (4.88 g) was dissolved in 20 ml of water and the solution was added to 2,176 g of 20% silica sol. To the stirred mixture, a solution of 213.1 g of ammonium paramolybdate in 640 ml of water was added. Thereafter, 281.2 g of an antimony tetroxide power, a solution of 232.8 g of nickel nitrate in 230 ml of water, a solution of 49.77 g of iron nitrate in 50 ml of water, and a solution of 89.63 g of bismuth nitrate in 89 ml of 10% nitric acid were added successively.

The resulting slurry was dried with a rotary disk type spray drier whose entrance and exit temperatures were controlled at 320° C. and 160° C., respectively. The dried particles were heated at 250° C., calcined at 400° C. for 2.5 hours and finally calcined at 570° C. for 3 hours to prepare a catalyst.

EXAMPLES 2 TO 11

A Catalysts having the compositions shown in Table 1 below were prepared as in Example 1.

EXAMPLE 12

A catalyst having the composition shown in Table 1 below was prepared as in Example 1 except that a solution of 2.08 g of sodium nitrate in 10 ml of water was added following potassium nitrate addition.

EXAMPLE 13

A catalyst having the composition shown in Table 1 below was prepared as in Example 1 except that 2.82 g of 85% orthophosphoric acid was added following the bismuth nitrate addition.

EXAMPLE 14

A catalyst having the composition shown in Table 1 below was prepared as in Example 13.

COMPARATIVE EXAMPLE 1

A catalyst having the composition shown in Table 2 below was prepared as in Example 1 except that potassium nitrate was not used.

COMPARATIVE EXAMPLES 2, 4, 6, 8 TO 11

Catalysts having the compositions shown in Table 2 below were prepared as in Example 1.

COMPARATIVE EXAMPLE 3

A catalyst having the composition shown in Table 2 below was prepared as in Example 1 except that bismuth nitrate was not used.

COMPARATIVE EXAMPLE 5

A catalyst having the composition shown in Table 2 below was prepared as in Example 1 except that iron nitrate was not used.

COMPARATIVE EXAMPLE 7

A catalyst having the composition shown in Table 2 below was prepared as in Example 1 except that antimony tetroxide was not used.

COMPARATIVE EXAMPLE 12

A catalyst having the composition shown in Table 2 below was prepared as in Example 1 except that cobalt nitrate was used in place of nickel nitrate.

Using the catalysts prepared in Examples 1 to 12 and Comparative Examples 1 to 12, vapor-phase catalytic ammoxidation of propylene was performed to produce acrylonitrile. The results obtained are shown in Tables 1 and 2 below.

TABLE 1

| Example No. | P | R | Mo | Bi | Fe | Sb | Ni | Si | Calcining Temperature (°C.) | Reaction Temperature (°C.) | Contact Time (sec) | Acrilonitrile Yield (%) | Propylene Conversion (%) |
|---|---|---|---|---|---|---|---|---|---|---|---|---|---|
| 1 | — | K 0.4 | 10 | 1.5 | 1.0 | 15 | 6.5 | 60 | 580 | 420 | 4.5 | 86.3 | 98.1 |
| 2 | — | K 0.05 | " | " | 1.5 | " | 6 | " | 590 | 410 | 4.5 | 84.2 | 98.0 |
| 3 | — | K 1.0 | " | " | 2.0 | " | 6 | " | 575 | 410 | 5.0 | 84.6 | 97.3 |
| 4 | — | K 0.2 | " | 0.5 | " | " | 5.5 | " | 550 | 415 | 4.5 | 83.3 | 98.5 |
| 5 | — | " | " | 2.5 | " | " | 5.5 | " | 600 | 410 | 5.5 | 84.1 | 98.7 |
| 6 | — | " | " | 1.0 | 0.5 | " | 7 | " | 590 | 405 | 5.5 | 83.7 | 97.8 |
| 7 | — | " | " | " | 2.0 | " | 7 | " | 650 | 420 | 4.0 | 84.8 | 98.3 |
| 8 | — | " | " | 1.5 | 1.5 | 8 | 6 | " | 580 | 420 | 4.5 | 85.0 | 98.5 |
| 9 | — | " | " | " | " | 25 | 6 | " | 580 | 420 | 4.5 | 85.3 | 98.4 |
| 10 | — | " | " | " | " | 15 | 4.5 | " | 510 | 420 | 5.0 | 84.1 | 98.3 |
| 11 | — | " | " | " | " | " | 7.5 | " | 690 | 420 | 5.0 | 83.5 | 98.6 |
| 12 | — | Na 0.2 K 0.2 | " | 1.0 | " | " | 6 | " | 570 | 420 | 4.5 | 85.0 | 98.5 |
| 13 | 0.2 | K 0.2 | " | " | " | " | 6 | " | 580 | 410 | 5.0 | 86.3 | 98.9 |
| 14 | 1.0 | " | " | " | " | " | 6 | " | 595 | 410 | 5.0 | 85.5 | 98.9 |

TABLE 2

| Comparative Example No. | P | R | Mo | Bi | Fe | Sb | Ni | Si | Calcining Temperature (°C.) | Reaction Temperature (°C.) | Contact Time (sec) | Acrylonitrile Yield (%) | Propylene Conversion (%) |
|---|---|---|---|---|---|---|---|---|---|---|---|---|---|
| 1 | — | — | 10 | 1.5 | 1.0 | 15 | 6.5 | 60 | 600 | 430 | 4.5 | 80.4 | 97.5 |
| 2 | — | K 2.0 | " | " | " | " | " | " | 550 | 410 | 6.0 | 80.5 | 98.5 |
| 3 | — | K 0.2 | " | — | 2.0 | " | 5.5 | " | 525 | 410 | 5.0 | 71.5 | 97.0 |
| 4 | — | " | " | 3.5 | " | " | " | " | 600 | 410 | 6.0 | 79.3 | 98.4 |
| 5 | — | " | " | 1.0 | — | " | 7 | " | 525 | 410 | 7.0 | 58.5 | 88.6 |
| 6 | — | " | " | " | 3.0 | " | 6 | " | 650 | 410 | 5.5 | 80.7 | 98.5 |
| 7 | — | " | " | 1.5 | 1.5 | — | 7.5 | " | 660 | 420 | 4.5 | 81.0 | 98.4 |
| 8 | — | " | " | " | 2.0 | 4 | 7 | " | 630 | 420 | 4.5 | 82.6 | 99.1 |
| 9 | — | " | " | " | " | 40 | " | " | 630 | 420 | 4.5 | 82.5 | 97.0 |
| 10 | — | " | " | " | " | 15 | 3.5 | " | 510 | 420 | 4.5 | 80.5 | 96.5 |
| 11 | — | " | " | " | 1.5 | " | 8.5 | " | 680 | 420 | 6.5 | 80.4 | 98.6 |
| 12 | — | K 0.4 | " | " | 1.0 | " | Co 6.5 | " | 530 | 410 | 6.0 | 81.1 | 97.3 |

As the results in Tables 1 and 2 above show, the Mo-Bi-Fe-Sb-Ni-Na and/or K based catalyst in accordance with the present invention is suitable for use in the production of acrylonitrile from propylene in that it has high reactivity with propylene and is capable of producing acrylonitrile in high yield. As a further advantage, this catalyst which does not contain any expensive component can be manufactured at a comparatively low cost. Therefore, in accordance with the process of the present invention, acrylonitrile can be produced with an industrial advantage by the vapor-phase ammoxidation of propylene.

While the invention has been described in detail and with reference to specific embodiments thereof, it will be apparent to one skilled in the art that various changes and modifications can be made therein without departing from the spirit and scope thereof.

What is claimed is:

1. A process for producing acrylonitrile by vapor-phase catalytic ammoxidation of propylene using a catalyst whose composition is represented by the empirical formula (I):

$$P_q R_r Mo_{10} Bi_a Fe_b Sb_c Ni_d O_e \qquad (I)$$

where

R is Na and/or K;

subscripts q, r, a, b, c, d and e represent atomic ratios, and when the atomic ratio of Mo is 10, q=0 to 3,
r=0.05 to 1.5,
a=0.1 to 3,
b=0.1 to 2.5,
c=5 to 30,
d=4 to 8, and
e=a number corresponding to the oxide formed by chemical combination of the components described in the formula (I) above.

2. The process of claim 1, wherein when the atomic ratio of Mo is 10, q=0 to 1.5, r=0.05 to 1.0, a=0.5 to 2.5, b=0.5 to 2, c=6 to 28, and d=4.5 to 7.5.

3. The process of claim 1, wherein R is K.

4. The process of claim 1, wherein R is Na and K.

5. The process of claim 1, wherein said catalyst is prepared by mixing the components required for said catalyst, drying said mixture and calcining said catalyst mixture in a non-reductive atmosphere at a temperature of about 200° to about 800° C. for a period of about 0.5 to about 10 hours.

6. The process of claim 1, wherein said catalyst is supported on a support as a catalyst carrier.

7. The process of claim 1, wherein in said ammoxidation, propylene, oxygen and ammonia are contacted with said catalyst and wherein the molar ratio of oxygen to propylene is about 1:1 to 4:1 and the molar ratio of ammonia to propylene is about 0.8:1 to about 3:1.

8. The process of claim 7, wherein the ammoxidation is conducted at a reaction temperature of about 380° to about 500° C. at a pressure of from an atmospheric pressure to about 3 kg/cm²·G and a catalyst contact time of from about 1 to about 30 seconds.

* * * * *